United States Patent [19]

Sykes et al.

[11] Patent Number: 4,600,786

[45] Date of Patent: Jul. 15, 1986

[54] ANTIBIOTIC OBAFLUROIN

[75] Inventors: Richard B. Sykes, Belle Mead; Adrienne Tymiak, Hopewell, both of N.J.

[73] Assignee: E. R. Squibb & Sons, Inc., Princeton, N.J.

[21] Appl. No.: 554,507

[22] Filed: Nov. 23, 1983

[51] Int. Cl.$^4$ .................................................. C07D 305/12
[52] U.S. Cl. ...................................... 549/263; 435/123; 435/253

[58] Field of Search ............................................ 549/263

Primary Examiner—Norma S. Milestone
Attorney, Agent, or Firm—Lawrence S. Levinson; Donald J. Barrack

[57] ABSTRACT

Cultivation of a strain of the microorganism *Pseudomonas fluorescens* A.T.C.C. No. 39502 yields a novel antibiotic substance 2,3-dihydroxy-N-[2-[(4-nitrophenyl)methyl]-4-oxo-3-oxetanyl]benzamide.

1 Claim, No Drawings

ANTIBIOTIC OBAFLUROIN

SUMMARY OF THE INVENTION

Cultivation of a strain of the microorganism *Pseudomonas fluorescens*, which has been deposited in the American Type Culture Collection as A.T.C.C. No. 39502 yields a novel antibiotic substance which has been designated obafluorin.

Obafluorin has been analyzed and found to be 2,3-dihydroxy-N-[2-[(4-nitrophenyl)methyl]-4-oxo-3-oxetanyl]benzamide, a compound having the formula

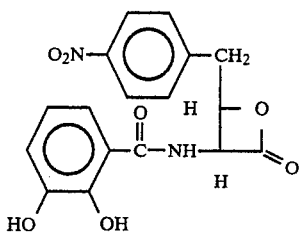

DETAILED DESCRIPTION OF THE INVENTION

The Microorganism

The microorganism used for the production of obafluorin is a strain of *Pseudomonas fluorescens*. A subculture of the microorganism can be obtained from the permanent collection of the American Type Culture Collection, Rockville, Md. Its accession number in the respository is A.T.C.C. No. 39502. In addition to the specific microorganism described and characterized herein, it should be understood that mutants of the microorganism (e.g., mutants produced through the use of x-rays, ultraviolet radiation, or nitrogen mustards) can also be cultivated to produce obafluorin.

Isolation of *Pseudomonas fluorescens* from a plant specimen (obtained in Princeton, N.J.) on which it is present can be accomplished by cutting the plant (leaves, stems and flowers) into small pieces under aseptic conditions. The plant pieces (2 g) are suspended in 100 ml of sterile diluent (NaCl, 8.5 g; $KH_2PO_4$, 0.3 g; $Na_2HPO_4$, 0.6 g; gelatin, 0.1 g; distilled water to 1 liter) and the suspension is shaken well. The aqueous layer is serially diluted using conventional techniques, plated and incubated at 37° C. for 1-2 days on McConkey's-Soil Extract agar which has the following composition:

| | |
|---|---|
| McConkey's Agar | 15.0 g |
| Soil Extract | 200.0 ml |
| Distilled water | 800.0 ml |
| Sterile 0.1% Biotin Solution* | 1.0 ml |
| Sterile 0.2% Thiamine Solution* | 1.0 ml |
| Sterile 1.0% Actidione Solution* | 10.0 ml |

*Added aseptically to the already sterile McConkey-Soil Extract Agar Medium.

*Pseudomonas fluorescens* A.T.C.C. No. 39502 is a gram negative rod occurring singly or as short, plump diplobacilli. Motility is achieved by means of 1 or more polar flagella.

The organism is oxidative both on Triple Sugar Iron Agar and Hugh-Leifson's O/F glucose test. It is cytochrome oxidase positive and is fluorescent on King's B medium. No pyocyanin pigment is produced on King's B medium. It is positive for catalase, arginine dihydrolase (Thrornley's method), and gelatinase. It forms levan from sucrose, lipase (with Tween 80 as substrate) and lecithinase (egg yolk as substrate). The organism does not hydrolyze starch or form indole or $\beta$-hydroxybutyrate. Growth occurs at 4° C., but not at 41° C.

The organism can utilize the following as sole carbon sources: DL-arginine, betaine, trehalose, m-inositol, l-arabinose, sucrose, propionate, and adonitol, but not butyrate or ethanol.

These characteristics agree with those of *Pseudomonas fluorescens* as set forth in Bergey's Manual of Determinative Bacteriology, 8th edition, editors Buchanan and Gibbons, Williams and Wilkins Co., Baltimore, Md., 1974, and serve to identify the producer of obafluorin as a strain of *Pseudomonas fluorescens*.

Production of the Antibiotic

*Pseudomonas fluorescens* A.T.C.C. No. 39502 produces the antibiotic obafluorin that possesses antibacterial activity. To form the antibiotic, *Pseudomonas fluorescens* A.T.C.C. No. 39502 is grown at, or near, room temperature (25° C.) under submerged aerobic conditions in an aqueous nutrient medium containing one, or more, assimilable carbon and nitrogen sources. The fermentation is carried out until substantial activity is imparted to the medium, usually about 15 to 18 hours, preferably about 17 hours.

After the fermentation has been completed, the broth and cells are separated. The supernate, acidified to about pH 3, is extracted with ethyl acetate saturated with water. The organic layer, containing the antibiotic, is dried in vacuo to an oily residue. The oily residue is redissolved in a small amount of a solvent mixture consisting of acetonitrile, water, and trifluoroacetic acid. The antibiotic is purified by chromatography on CHP20P resin with the solvent mixture as developing solvent.

The following example further illustrates the preparation and isolation of obafluorin.

EXAMPLE

Yeast-extract, beef-extract, NZ amine A, glucose agar slants were seeded with *Pseudomonas fluorescens* A.T.C.C. No. 39502. They were incubated for 48 hours at 25° C. and then used to inoculate 100 ml of medium contained in each of two B 500 ml Erlenmeyer flasks. The composition of the germination medium was:

| | Grams |
|---|---|
| Yeast Extract | 5.0 |
| Glucose | 5.0 |
| $MgSO_4.7H_2O$ | 0.1 |
| $FeSO_4.7H_2O$ | 0.1 |
| Soil Extract Filtrate* | 200 ml |
| Tap Water | 800 ml |

*The soil extract is made by extracting 1 volume of soil with 2 volumes of water at 100° C. for 1 hour, at which time the suspension is filtered. The filtrate is added to the medium as required.

The medium was sterilized at 121° C. for 30 minutes and 15 lbs. steam pressure before use. The inoculated germination flasks were incubated at 25° C. for 24 hours on a rotary shakes, operating at 300 rpm with a 2 inch throw.

A 1% (v/v) transfer was made from the germination flasks to fifty 500 ml Erlenmeyer flasks, each containing 100 ml of the same medium as used for the germinators.

These flasks were incubated at 25° C. on a rotary shakes, operating at 300 rpm with a 2 inch throw for 17 hours, at the end of which time the antibiotic was formed. The antibiotic was detected by conventional paper-disc agar-diffusion assay against *Bacillus licheniformis* SC*9262.

*SC refers to the culture collection of E. R. Squibb & Sons, Inc., Princeton, N.J.

The fermentation broth was pooled and the pool was centrifuged at 62,500 g to sediment the bacteria. The supernate (4.9 liters), adjusted to pH 3 by the addition of 37% HCl (2 ml), was extracted three times with 175 ml portions of water-saturated ethyl acetate. The organic extracts were pooled and concentrated in vacuo to a residue. The residue was suspended in 15 ml of acetonitrile and the soluble material was dried in vacuo to an oily residue (459.3 mg).

The oily residue was dissolved in 4.6 ml of an acetonitrile-water-trifluoroacetic acid mixture (55:45:0.1, v/v) and chromatographed, one half portion at a time, on a 90 ml column of 75–150μ Diaion CHP20P** resin with the same solvent mixture. Fractions from both columns that showed antibacterial activity vs. *Bacillus licheniformis* SC 9262 were pooled and dried in vacuo to yield 139.4 mg of cream-colored, amorphous obafluorin.

**Diaion CH20P is macroreticular styrene-divinylbenzene copolymer beads, Mitsubishi Chemical Company, Ltd., Japan.

CHARACTERISTICS OF OBAFLUORIN

The amorphous solid was characterized: melting point 109°–113° C.; $[\alpha]_D^{25} + 116°$ (c 0.10, acetonitrile) UV (EtOH) 215 ($E_1{}_{cm}^{1\%}$ 970), 258 (520), 325 (160) nm; UV (EtOH/H$^+$) 258 (430), 325 (100) nm; UV (EtOH/OH$^-$) 275 (480), 330 (200) nm; IR (CH$_3$CN) 3360, 1840, 1650, 1600, 1530, 1350, 1270, 1240 cm$^{-1}$; $^1$H NMR (CD$_3$CN) δ11.7 (1H, broad), 8.12 (1H, d, J=8 Hz), 8.09 (2H, d, J=8.8 Hz), 7.51 (2H, d, J=9.1 Hz), 7.17 (1H, dd, J=8.1, 1.1 Hz), 7.04 (1H, dd, J=8.1, 1.1 Hz), 6.82 (1H, dd, J=8.8 Hz), 6.8 (1H, broad), 5.74 (1H, dd, J=8, 6.5 Hz), 5.05 (1H, m), 3.37 (1H, dd, J=15, 9.1 Hz), 3.20 (1H, dd, J=15, 5.1 Hz), $^{13}$C NMR (CD$_3$CN) δ170.5, 168.2, 149.5, 147.3, 146.3, 144.7, 130.5 (2C), 124.0 (2C), 119.8, 119.5, 114.4, 78.0, 59.6, 36.0; $^{13}$C NMR (CD$_3$COCD$_3$) δ169.3, 166.8, 148.6, 146.2, 145.5, 143.8, 129.5 (2C), 122.7 (2C), 118.7, 118.1, 116.7, 113.3, 76.8, 58.5, 34.9; FABMS (-ion, TMSO) 717 (2M-H), 733 (2M+H$_2$O-H), 375 (M+H$_2$O-H), 357 (M-H), 313 (M-CO$_2$-H) m/z; HRFABMS (-ion) 357.080 amu (C$_{17}$H$_{13}$N$_2$O$_7$ requires 357.072 amu).

ANTIBACTERIAL ACTIVITY OF OBAFLUORIN

Obafluorin was dissolved in acetonitrile to a concentration of 1 mg/ml. Discs of Whatman No. 4 filter paper (6.3 mm diameter) were loaded with 10 μl of the solution, air dried, and then placed on the surface of nutrient agar plates inoculated with the test strains in Petri dishes. After incubation at 37° C. for 24 hours, the plates were examined for antibiotic activity. The results are shown below.

| Organism | SC Number | Diameter (mm) Zone of Inhibition |
|---|---|---|
| Staphylococcus aureus | 1276 | 8.7 |
| Staphylococcus aureus | 2399 | 7.4 |
| Staphylococcus aureus | 2400 | 7.9 |
| Bacillus licheniformis | 9262 | 14.0 |
| Sarcina lutea | 2495 | 10.0 |
| Escherichia coli | 10,857 | 10.5 |
| Escherichia coli | 10,896 | 12.8 |
| Escherichia coli | 10,909 | 13.4 |
| Enterobacter cloacae | 8236 | 9.3 |
| Proteus rettgeri | 8479 | 7.7 |
| Pseudomonas aeruginosa | 9545 | 9.1 |

What is claimed is:

1. 2,3-Dihydroxy-N-[2-[(4-nitrophenyl)methyl]-4-oxo-3-oxetanyl]benzamide.

* * * * *

UNITED STATES PATENT AND TRADEMARK OFFICE
CERTIFICATE OF CORRECTION

PATENT NO. : 4,600,786

DATED : July 15, 1986

INVENTOR(S) : Richard B. Sykes et al.

It is certified that error appears in the above-identified patent and that said Letters Patent is hereby corrected as shown below:

The title should be -- Antibiotic Obafluorin --.

Column 2, line 47, delete "B".

Signed and Sealed this

Seventh Day of October, 1986

[SEAL]

Attest:

DONALD J. QUIGG

Attesting Officer

Commissioner of Patents and Trademarks